United States Patent [19]

Visser et al.

[11] Patent Number: 5,789,388
[45] Date of Patent: *Aug. 4, 1998

[54] VACCINE AGAINST VIRUSES ASSOCIATED WITH ANTIBODY-DEPENDENT-ENHANCEMENT OF VIRAL INFECTIVITY

[75] Inventors: Nicolaas Visser; Petrus Alphonsus Maria van Woensel, both of Boxmeer, Netherlands; Thomas Christoph Mettenleiter, Tuebingen, Germany

[73] Assignee: Akzo Nobel N.V., Arnhem, Netherlands

[*] Notice: The term of this patent shall not extend beyond the expiration date of Pat. No. 5,626,850.

[21] Appl. No.: 359,980

[22] Filed: Dec. 20, 1994

[30] Foreign Application Priority Data

Dec. 21, 1993 [EP] European Pat. Off. ............. 93203614

[51] Int. Cl.$^6$ ........................................ C12N 15/00
[52] U.S. Cl. ................ 514/44; 424/199.1; 424/93.1; 424/93.2; 435/320.1; 435/325
[58] Field of Search ................ 435/320.1, 240.2, 435/325; 514/44; 424/93.3, 93.2, 93.1, 199.1

[56] References Cited

U.S. PATENT DOCUMENTS

| 5,240,703 | 8/1993 | Cochran | 424/89 |
| 5,626,850 | 5/1997 | Visser et al. | 424/199.1 |
| 5,674,500 | 10/1997 | Peeters et al. | 424/199.1 |

FOREIGN PATENT DOCUMENTS

| WO 92/05263 | 4/1992 | WIPO. |
| WOA 94 01573 | 1/1994 | WIPO. |

OTHER PUBLICATIONS

Report and recommendations of the panel to assess the NIH investment in research on gene therapy. Available on the NIH home page @ www.nih.gov., Dec. 7, 1995.

B. Peeters et al., "Pseudorabies Virus Envelope Glycoproteins gp50 and gII Are Essential for Virus Penetration, but Only gII Is Involved in Membrane Fusion," J. Virol., vol. 66 No. 2, pp. 894–904, Feb. 1992.

C. Marchioli et al., "Evaluation of pseudirabies virus glycoprotein gp50 as a vaccine for Aujesky's disease in mice and swine," J. Virol., vol. 61, No. 12, pp. 3977–3982, 1987.

D. Johnson et al., "Herpes Simplex viruses lacking glycoprotein D are unable inhibit virus penetration," J. Virol. vol. 62, No. 12, pp. 4605–4612, 1988.

B. Peeters et al., "Envelope glycoprotein gp50 of pseudorabies virus is essential for virus entry," J. Virol., vol. 67, No. 1, pp. 170–177, 1993.

I. Rauh et al., "Pseudorabies glcoproteins gII and gp50 are essential for virus penetration," J. Virol., vol. 65, No. 10, pp. 5348–5356, 1991.

N. De Wind et al., "Linker insertion mutagenesis of herpesvirus," J. Virol. vol. 64, No. 1o, pp. 4691–4696, 1990.

S. Heffner et al., "Glycoprotein pg50 negative pseudorabies virus," J. Virol., vol. 67, No. 3, pp. 1529–1537, 1993.

W.E. Robinson et al., "Antibody–dependent enhancement of human immunodeficiency virus type 1 (HIV–1) infection in vitro by serum from HIV–1 infected and passively immunized chimpanzees," *Proceedings of the National Academy of Science of US*, 86:12, Jun. 1989 pp. Apr. 10–Apr. 14, Washington DC.

*Primary Examiner*—Jasemine C. Chambers
*Assistant Examiner*—Deborah J. R. Clark
*Attorney, Agent, or Firm*—Mary E. Gormley

[57] ABSTRACT

The present invention relates to a vaccine against a virus associated with antibody-dependent-enhancement of viral infectivity. Such a vaccine comprises a herpesvirus vector which is able to spread from cell-to-cell and which does produce non-infectious progeny virions having a gene encoding an antigen of said virus inserted into the herpesvirus genome.

6 Claims, 4 Drawing Sheets

VACCINE AGAINST VIRUSES ASSOCIATED WITH ANTIBODY-DEPENDENT-ENHANCEMENT OF VIRAL INFECTIVITY

FIELD OF THE INVENTION

The present invention relates to a live virus vector which is able to spread from cell-to-cell and which produces non-infectious progeny virions, to a cell culture comprising such a live virus vector and to vaccines based on this live virus vector.

BACKGROUND OF THE INVENTION

The majority of viral infections of animals and man are not fatal, but are followed by recovery and the development of a state of relative or absolute resistance against re-infection with the same virus. Much of this resistance can be attributed to specific antiviral antibodies, although cellular immune mechanisms also contribute to the protection of the host. Viruses are complex antigens, and as such can be expected to stimulate the production of antiviral antibodies against a variety of different antigenic determinants or epitopes. Not all antiviral antibodies are necessarily virus neutralizing antibodies (Porterfield J. S., Advances in Virus Research 31, 335–355, 1986). However, in addition to these virus neutralizing antibodies or non-neutralizing antibodies a further group of antibodies exist: antibodies which enhance the infectivity of the virus. This phenomenon is known as antibody-dependent-enhancement (ADE) of viral infectivity and has been observed with various macrophage-infecting viruses.

ADE of virus infection occurs when monocytes or macrophages are more efficiently infected by complexes of virus plus antibody than by virus alone. ADE of virus infection in vitro or in vivo has been reported for a wide range of viruses, such as various flaviviruses, including Dengue virus, West Nile virus, Murray Valley encephalitis virus and Yellow fever virus; alphaviruses such as tick-borne encephalitis virus, Semliki Forest virus, Western equine encephalitis virus and Sindbis virus; Lactate dehydrogenase virus (family Togaviruses); human respiratory syncytial virus; influenza A virus, rabies virus, feline infectious peritonitis virus (FIPV), human- and feline immunodeficiency virus (HIV, FIV) and murine cytomegalo virus (review of Porterfield 1986, supra; Olsen, C. W., Veterinary Mircobiology 36, 1–37, 1993).

Of course for those viruses associated with ADE of viral infectivity for which alteration of the pathogenesis of the disease in vivo occurs, ADE has an important bearing on the development of vaccines for these viruses, because the pre-existence of enhancing antibodies due to the vaccination with viral antigens may accelerate infection and the onset of disease once the vaccinated host becomes infected with a virus in the field.

For example the "early death" syndrome has been reported in cats after challenge of cats vaccinated with a live vaccinia virus capable of expressing the FIPV spike protein: kittens vaccinated with the recombinant vaccinia virus died earlier than non-vaccinated animals whereas vaccinated kittens that survived the challenge had suffered from a form of FIP much more severe than naturally occurring FIP (Vennema H. et al., J. Virology 64, 1407–1409, 1990).

Concerning the mechanisms involved in ADE it is suggested that enhancing antibodies complexed with the virus facilitate the binding to the virus to cells, macrophages and monocytes, bearing receptors for the Fc portion of immunoglobulins or receptors for complement components. The increased binding of the virus-antibody complex to the receptors then leads to an increased infectivity (Porterfield, J. S., 1986, supra).

Therefore, there is a strong desire to develop a vaccine effective against a virus associated with ADE of viral effectivity which when presented to the immune system of a host induces a protective immune response without the concomitant induction of antibodies.

Recently, a new generation of live herpesvirus vaccines based on a novel approach has been disclosed by Heffner, S. et al. (J. Virology 67, 1529–1537, 1993) and Peeters, B. et al. (J. Virology 67, 170–177, 1993). It has been demonstrated therein that glycoprotein gp50, the homolog of the HSV glycoprotein gD, which represents a constituent of the virion envelope of the herpesvirus pseudorabies virus (PRV), is indispensable for infectivity of free PRV virions. Virions lacking gp50 are noninfectious due to a defect in penetration into target cells. Virus mutants deficient in gp50 expression can be isolated on genetically engineered cell lines that stably carry the viral gp50 gene in their chromosomal DNA and express this gene during infection by gp50⁻PRV leading to phenotypic complementation of the genetic defect. The resulting virions carry gp50, provided by the cell line, in their envelope and are fully infectious, the so-called null-viruses.

However, after infection of non-complementing cells gp50 is lost and, consequently, virions released from these cells are noninfectious. Importantly, gp50 is not required for direct viral cell-to-cell spread, which means that after primary infection by phenotypically complemented virions, virus spread can occur solely by direct cell-to-cell transmission.

Alternatively, this effect could also be achieved using PRV mutants deficient in gp50 expression which were not phenotypically complemented but which were in a cell-associated form.

On the basis of the above described gp50⁻PRV mutants safe live vaccines were devised which replicated only in the vaccinated host and did not spread to other animals yet were able to induce protective immunity in the vaccinated host.

SUMMARY OF THE INVENTION

The present invention now provides a new concept which overcomes the problems encountered with the development of vaccines against viruses associated with ADE of viral infectivity: the use of a live virus which is able to spread from cell-to-cell and which produces non-infectious progeny virions as a vector for a gene encoding an antigen of a virus associated with ADE of viral infectivity. Such vector viruses may be derived from herpesviruses or pox viruses, such as vaccinia.

In particular, it has now been found that if a live herpesvirus which is able to spread from cell-to-cell and which produces non-infectious progeny virions is administered to the host via the intra-nasal route or via the parenteral route in a cell-associated form, significant protection is induced against that herpesvirus without the concomitant induction of humoral antibodies.

FIG. 1.

Genomic map of US region of the PRV parent strain, the quadruple mutant, and the PRV gene fragment stably transformed into the MDBK cell line.

FIG. 2.

Relative growth of the pigs vaccinated with the quadruple PRV mutant, cell-associated PRV mutant and unvaccinated pigs from 8 days before to 11 days after challenge (group

3

1=Quad IN, group 2=Quad IM, group 3=cell IM 5.5, group 4=cell IM 4.0, group 5=control).

FIG. 3.

Virus neutralizing antibody titres of blood samples taken from pigs from 3 weeks before to 3 weeks after challenge. The designation of the groups is the same as in FIG. 2.

FIG. 4.

Genomic map of $U_s$ region of the PRV mutant PRVQ-6 comprising the PRRSV ORF 7 insert.

DETAILED DESCRIPTION OF THE INVENTION

Figure 1:
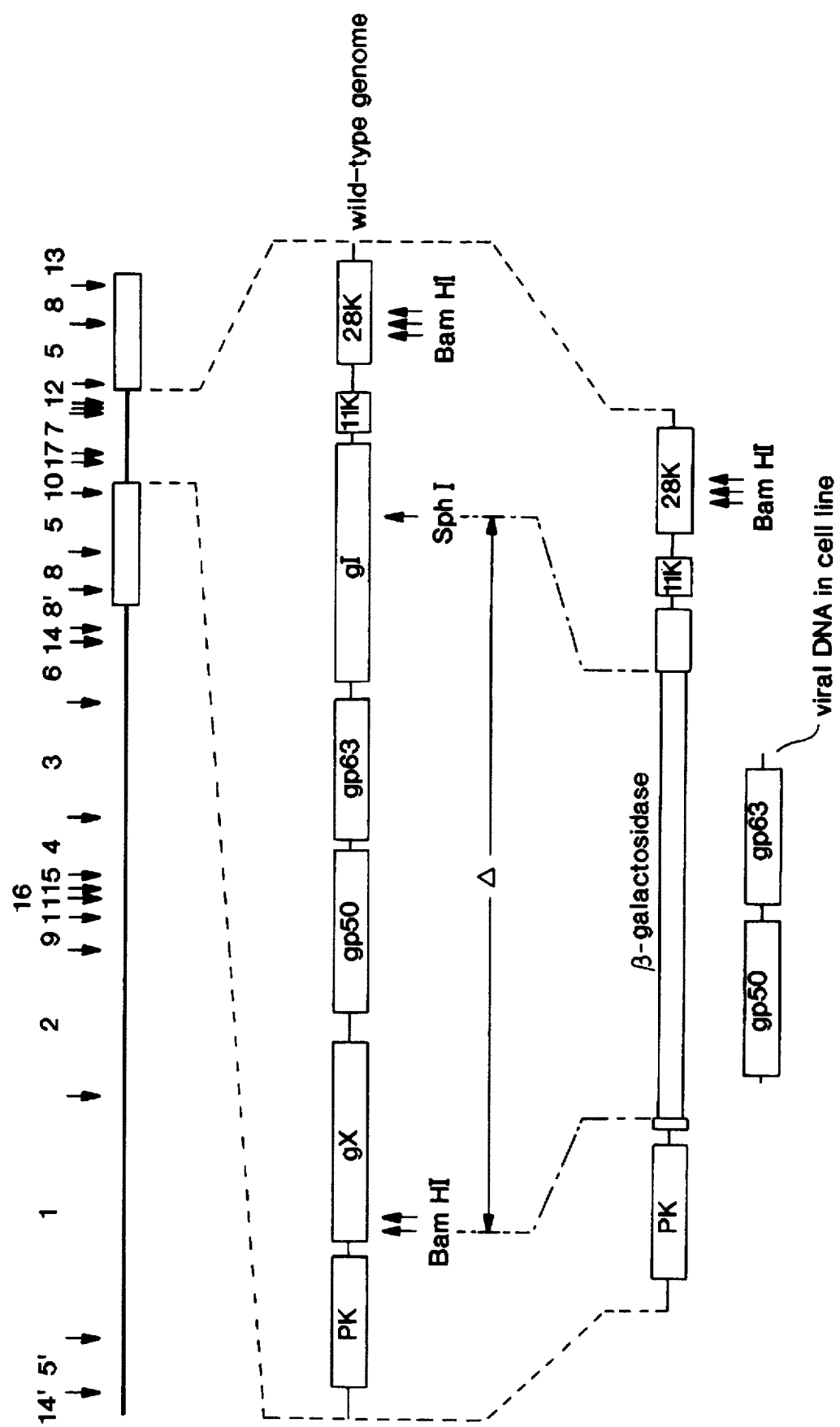

The invention therefore relates to such a live virus, in particular to a herpesvirus as a vector harbouring a gene encoding an antigen of a virus associated with antibody-dependent enhancement (ADE) of viral infectivity.

Such a live herpesvirus vector can be a virus that is deficient in expression of a viral protein responsible for entry into target cells, as a result of a mutation in the gene encoding said viral protein yet retains its property to spread from cell-to-cell, said virus being phenotypically complemented for that genetic defect, the so-called null-virus.

A mutation is understood to be a change of the genetic information in said gene with respect to the genetic information present in this gene in the naturally occurring virus.

The mutation is, in particular, a nucleic acid substitution, deletion, insertion or inversion, or a combination thereof resulting in a herpesvirus mutant which fails to produce a functional viral protein responsible for entry into target cells.

Alternatively, a live herpesvirus vector with the desired properties can be a virus that has the same genetic defect as defined above without the phenotypic complementation, but which virus is in a cell-associated form.

The characteristics of the herpesviruses on which the present vector are based and their preparation are outlined in the prior art (Heffner et al., 1993, supra; Peeters et al., 1993 supra; international patent application no PCT/NL93/00146 and PCT/EP93/ 01661).

Preferably, the genetic defect in the herpesvirus vector resulting in the inability of the vector to express the viral protein responsible for entry of the virus into the target cells is obtained by inserting a foreign DNA sequence into the gene encoding said viral protein (insertional inactivation) and/or by deleting all or part of said gene.

The herpesvirus vector according to the present invention can be derived from any herpesvirus displaying the desired properties outlined above. Preferably the herpesvirus vector is selected from the group of herpesviruses consisting of herpes simplex virus (HSV) varicella-zoster virus (VZV), human cytomegalovirus (HCMV), pseudorabies virus (PRV), feline herpesvirus (FHV), bovine herpesvirus (BHV) and equine herpesvirus (EHV).

In a preferred embodiment of the invention a live herpesvirus vector is provided wherein the herpesvirus is a pseudorabies virus.

A pseudorabies virus vector with the desired properties mentioned above can be a pseudorabies virus which is not able to express (functional) glycoprotein gp50 as a result of a mutation in the gene encoding gp50, i.e. the pseudorabies virus is genotypically gp50⁻, but which is complemented with the gp50 glycoprotein, i.e. the pseudorabies virus is phenotypically gp50⁺.

Alternatively, a suitable pseudorabies virus vector is genotypically gp50⁻ and is in its cell-associated form.

4

In the live herpesvirus vector according to the invention the gene encoding the antigen of a virus associated with ADE of viral infectivity is inserted into a non-essential region of the herpesvirus, i.e. a region which can be used for the incorporation of said gene without disrupting essential functions of the herpesvirus such as those necessary for infection or replication of the virus. Such regions are generally known in the art for herpesviruses.

For example, for PRV several non-essential regions have been disclosed, such as the genes encoding gp50, gp63, gI, gIII, gX, IIK, thymidine kinase (TK), ribonucleotide reductase (RR), protein kinase (PK) or 28K (Peeters et al., 1993, supra; de Wind, N. et al., J. Virol 64, 4691–4696, 1990; Moorman, R. J. M. et al., J. Gen Virol 71, 1591–1595, 1990; Petrovskis, E. A. et al., Virology 159, 193–195, 1987; van Zijl, M. et al., J. Gen. Virol 71, 1747–1755, 1990; Thomsen, D. R. et al., Gene 57, 261–265, 1987; Keeler, C. L. et al., Gene 50, 215–224, 1986; Whealey, M. E. et al., J. Virol 62, 4185–4194, 1988; van Zijl, M. et al., J. Virol 65, 2761–2765, 1991; Mettenleiter, Th.C. et al., Virology 179, 498–503, 1990; U.S. Pat. No. 4,609,548, European patent no 0263207), for HSV e.g. TK (Shih, M-F et al., Proc. Natl. Acad. Sci.: 81, 5867–5870, 1984, for VZV e.g. TK (Lowe, R.S. et al., Proc. Natl. Acad. Sci. 84, 3896–3900, 1987; for HCMV e.g. β-gene (Spaete, R. R. et al., Proc. Natl. Acad. Sci. 84, 7213–7217, 1987; for BHV-1 e.g. TK and gIII (Kit, S. et al., Arch. Virol 124, 1–20, 1992; Kit, M. et al., Vaccine 9, 564–572, 1991), for FHV e.g. TK (Cole, G. E. et al., J. Virol 64, 4930–4938, 1990).

Well-known procedures for inserting DNA sequences into a cloning vector and in vivo homologous recombination or cosmid cloning techniques can be used to insert the gene into the non-essential region of the herpesvirus genome (Maniatis, T. et al. (1982) in "Molecular cloning", Cold Spring Harbor Laboratory; European patent application no. 074808; Roizman, B. and Jenkins, F. J., Science 229, 1208, 1985; Higuchi, R. et al., Nucleic Acids Res. 16, 7351, 1988, de Wind, N. et al., J. Virol. 64, 4691–4696,. 1990; van Zijl, M. et al., J. Virol. 62, 2191–2195, 1988; Ackermann, M., J. Vet-Med. B., 35, 379–396, 1988, and methods described in the paragraph above).

An essential requirement for the expression of the heterologous gene by the herpesvirus vector according to the invention is an adequate promoter operably linked to the heterologous gene. It is obvious to those skilled in the art that the choice of a promoter extends to any eukaryotic, prokaryotic or viral promoter capable of directing gene transcription in cells infected by the herpesvirus vector, e.g. promoters of the retroviral long terminal repeat (Gorman et al., Proc. Natl. Acad. Sci. USA 79, 6777–6781, 1982), the SV40 promoter (Mulligan and Berg, Science 209, 1422–1427, 1980), the cytomegalovirus immediate early promoter (Schaffner et al., Cell 41, 521–530, 1985), the β-globin promoter (Smiley, J. R. et al.) J. Virol, 61, 2368–2377, 1987), Kriegler, M. In: Gene transfer and expression: a laboratory manual, 3–81, ed. Kriegler M., Freeman and Company, New York, 1990, in addition to the promoters of the herpesvirus genes.

The gene encoding the antigen of a virus associated with ADE of viral infectivity inserted into the herpesvirus vector according to the invention can be derived from any of these viruses for which protection by means of vaccination is sought and which encodes an antigen that is capable of triggering a protective immune response in the vaccinate.

A list of viruses associated with ADE of viral infectivity for which a vaccine based on a live herpesvirus vector according to the invention can be developed is given above.

Preferably, the live herpesvirus vector according to the invention comprises a gene encoding an antigen of a virus selected from the group consisting of FIPV porcine reproductive and respiratory syndrome virus (PRRSV), equine arteritis virus (EAV), African swine fever virus, FIV and HIV.

Most preferred are live herpesviruses according to the invention comprising a gene encoding an antigen of FIPV or PRRSV.

In the case of insertion of a PRRSV gene into the herpesvirus vector, said gene preferably is an open-reading-frame (ORF) selected from the group consisting of ORF 2 to 7, ORF 4,5 or 7 being most preferred (Conzelmann, K-K et al., Virology 193, 329–339, 1993; international patent application WO 92/21375).

Relevant antigens of viruses associated with ADE of viral infectivity which may be expressed by the herpesvirus vector include for example for FIPV: spike (S) protein, membrane (M) protein and nucleocapsid (N) protein (Vennema, H. et al., J. Virol 64, 1407–1409, 1990; Vennema, H. et al., Virology 181, 327–335, 1991) for PRRSV: ORFs 2–7, in particular ORF 4,5 or 7 (Conzelmann et al., 1993, supra; international patent application WO 92/21375, for HIV and FIV surface/envelope proteins, for African swine fever virus envelope glycoproteins and for equine arteritis virus ORF 4 or ORF 5.

Furthermore, the present invention also provides a vaccine for the protection of a host against a virus associated with ADE of viral infectivity for intranasal administration which comprises the herpesvirus vector described above, and a pharmaceutically acceptable carrier or diluent.

The invention further provides a vaccine against the said viruses which comprises infected cells derived from the cell culture containing the described herpesvirus in a cell-associated form in addition to a pharmaceutically acceptable carrier or diluent.

Pharmaceutical acceptable carriers or diluents for intranasal administration or for parenteral administration of cell-associated virus vaccines are well known to those of skill in the art.

Usually, cell-free herpesviruses are stored in a lyophilized form in the presence of stabilizers until use. The vaccine is then reconstituted prior to administration with the carrier or diluent, such as water, buffered saline, alcohols, polyols such as glycerol or oil-emulsions.

If desired, the vaccine according to the invention is formulated with one or more adjuvants. Suitable examples are saponins such as Quil A, aluminium hydroxide, cholera- or tetanus toxoid, oil-emulsion (o/w or w/o) and aqueous vitamin-E dispersion.

Optionally, stabilizers such as citric acid, preservatives such as thimerosal, merthiolate and gentamicin may be added.

Such formulations may be administered intranasally as an aerosol or spray or as liquid drops.

The preparation of cell-associated herpesvirus vaccines is well known and commercially generally used for Marek's disease virus vaccines.

In the present invention the herpesvirus vector in its cell-associated form can, for example, be obtained by infecting a non-complementing cell culture with the null virus, or by transfecting a non-complementing cell culture with the genomic DNA of the herpesvirus vector having the genetic defect defined above. Suitable cell cultures for propagating the herpesvirus vector can be derived from ape cells (vero cells), porcine cells (SK6), hamster cells (BHK) and bovine cells (MDBK).

After culturing for a sufficient period infected cells can be removed from the culture using phosphate buffer to which trypsin has been added. Subsequently, pelleted cells can be resuspended in freezing medium which may be composed of cell growth medium with the addition of DMSO (7.5–15%). The vaccine is normally stored and transported in liquid nitrogen at $-196°$ C. Before use a volume of a well known diluent ranging from cell culture medium to buffered saline with a proteinaceous additive such as lactalbumin hydrolysate can be added to the vaccine.

The vaccine is administered in an effective dosage of the vector virus, i.e. an amount of the live herpesvirus vector that will induce immunity in the vaccinate against challenge by a virulent virus associated with ADE of viral infectivity.

A typical dose is $10^2$–$10^7$ TCID$_{50}$ in a volume of 0.5 to 1.5 ml.

EXAMPLE 1
Vaccination with PRV gp50 mutant
Vaccines a) The quadruple PRV deletion mutant having a deletion in the U$_s$ region spanning the gX, gp50, gp63 and gI genes is grown on MT50-3 cells (Rauh, L et al., J. Virol 65, 5348–5356, 1991) which are complementing for the gp50 protein product. A dose of $10^5$ TCID$_{50}$ per animal is used. The construction of the quadruple PRV deletion mutant is carried out using conventional recombinant DNA techniques (internatinnal application PCT/EP93/01661) and is summarized in FIG. 1.

b) The same virus is grown and maintained in Vero cells. An equivalent amount of virus as above calculated to be present intracellularly is prepared as a dosage per animal.

Vaccinations

The pigs 4–5 weeks of age are divided over 5 groups.

Group 1 (7) receiving vaccine a) intranasally

Group 2 (7) also receives vaccine a) but intramuscularly (2 ml).

Group 3 (7) receives vaccine b) intramuscularly ($10^{5.5}$ cell/dose)

Group 4 (7) receives vaccine b) intramuscularly ($10^4$ cell/dose)

Group 5 (5) untreated animals as controls. The intranasal administration is done by giving 1 ml of vaccine into each of the nostrils.

Challenge

Three weeks after the vaccination all the pigs are challenged intranasally with $10^7$TCID$_{50}$ of strain 75V19.

Serology

Blood samples are taken at 0, 3, 4, 5 and 7 weeks after vaccination. Serum is tested in the VN-test.

Results

Growth rates

Figure 2:
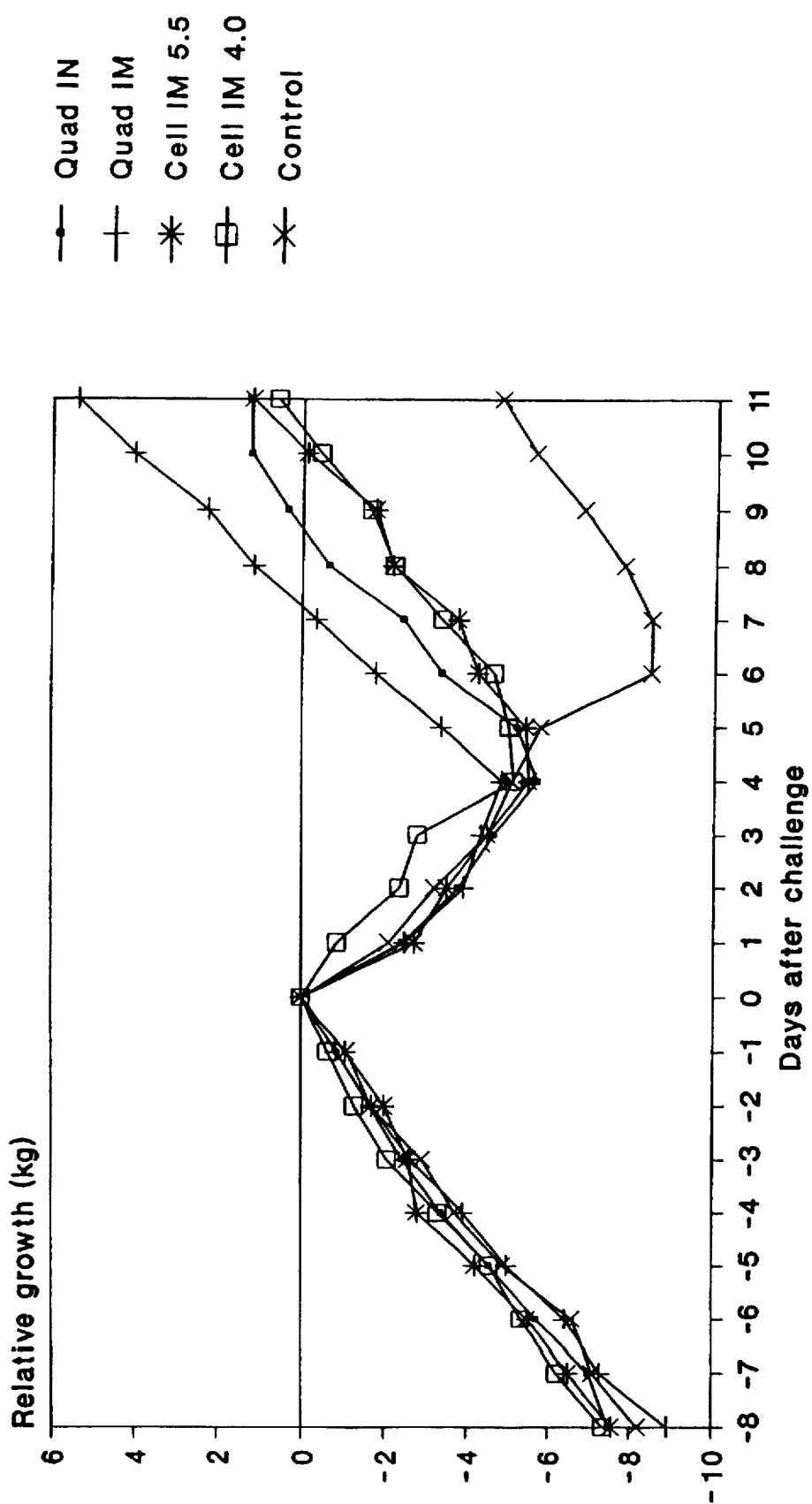

The vaccination protected the respective groups significantly against the very severe drop in body weights for more than 14 days as observed in the control pigs (FIG. 2.).

Group 2 had retained after about 7 days their weights at time of challenge. Group 1 after 8 days and Group 3 and 4 needed 9–10 days. For each group the growth rates relative to the time of challenge are presented in FIG. 2.

Serology

Figure 3:
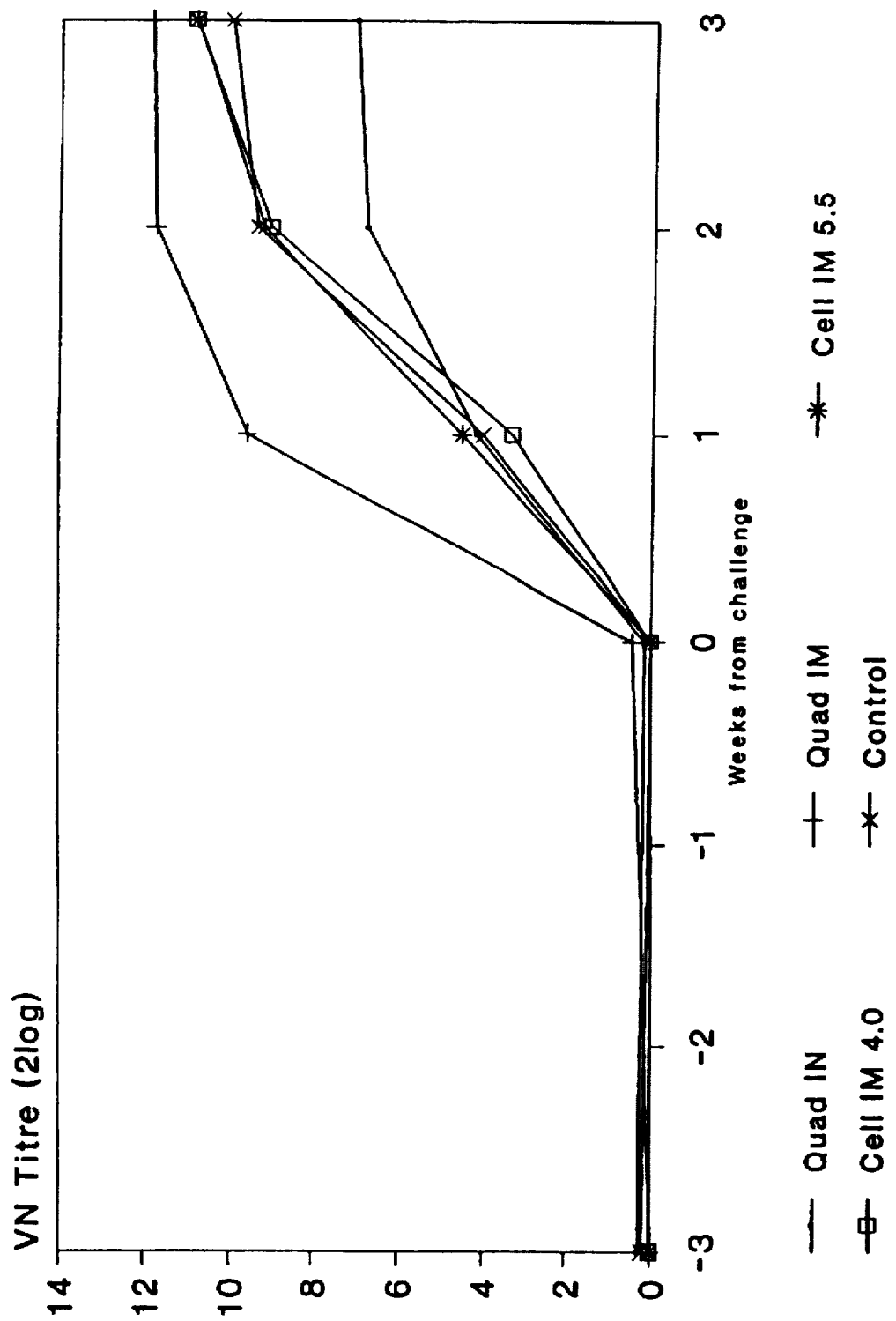

VN titres were measured in each of the groups at time points indicated in FIG. 3. Two-fold serial tions are prepared and incubated with 100 TCID$_{50}$ pseudorabies for 24 hours at 37° C. Then the virus-serum mixtures are seeded onto Vero cells and CPE is after 4 days incubation at 37° C. in a $CO_2$ incubator.

Only the pigs of Group 2 showed VN titres without and especially in the presence of complement (Table 1) at time of challenge. This observation is confirmed after challenge where again only Group 2 showed within a week a quick classical booster response, whereas all the other groups showed a delayed response very similar to the naive control group. Surprisingly the intranasally inoculated Group 1 even revealed a lower VN response than the controls.

From the serological results together with the protection data it is clear that the intranasal vaccination with null-virus and also cell-associated gp50⁻virus in a dose-dependent way showed significant protection in the absence of neutralising (±C') antibodies.

TABLE 1

| Animals of Group 2 | VN | |
|---|---|---|
| | -C' | +C' |
| 81 | 0 | 0 |
| 82 | 0 | 3 |
| 83 | 0 | 3 |
| 84 | 1 | 3 |
| 85 | 2 | 5 |
| 86 | 0 | 0 |
| 87 | 0 | 2 |

EXAMPLE 2

Cloning of the PRRSV ORF 7 in the quadruple mutant

The plasmid pBluescript SK$^+$ (Stratagene #212205) was cut with HinCII and BamHI the ends were dephosphorylated with alkaline phosphatase. From a cloned SphI fragment of the US region of PRV, containing the ORF's for gX, gp50, gp63 and part of gI and PK, the SphI, BamHI fragment, containing part of the ORF for PK and gX, was then cloned into the pBluescript SK$^+$ vector. This was done by first performing a digestion with SphI, filling in the ends with Klenow and then performing a digestion with BamHI. The remaining fragment was isolated from an agarose gel and cloned into the vector with T4 DNA ligase, creating the plasmid pBgX. To generate a multiple cloning site after the gX sequence the plasmid pBgX was cut with XbaI and the ends were filled in with Klenow, then the plasmid was further cut with BamHI and the ends were dephosphorylated with alkaline phosphatase. From the original plasmid pBluescript SK$^+$ the BamHI HincII fragment was isolated by digestion with BamHI and HincII and isolated from an agarose gel. This fragment, containing a large part of the multiple cloning site of pBluescript was then ligated in the pBgX vector with T4 DNA ligase creating the pBgX$^+$ vector. The ORF 7 of PRRSV was then cloned into the pBgX$^+$ vector by digesting the vector with PstI, filling in the ends with Klenow and dephosphorylation with alkaline phosphatatase. From the plasmid pPRRSV-T1, containing all structural genes of PRRSV (Conzelmann et al., 1993, supra) the ORF 7 was isolated by a double digestion with HincII and SmaI, the ORF 7 containing 0.52 kb fragment was isolated from an agarose gel and cloned into pBgX+ with T4 DNA polymerase generating the plasmid pBX7. To generate 3' homology with the US region of PRV the vector pBX7 was cut with EcoRV and the ends were dephosphorylated with alkaline phosphatase. A SphI BamHI fragment from the US region of PRV, containing the 11K gene and part of the gI and 28K genes, was made blunt by filling in the ends with Klenow and cloned into pBX7 with T4 DNA polymerase. After the orientation of the inserts was checked this plasmid, pBQ7, containing part of the PRV PK gene, part of the PRV gX gene, the PRRSV ORF 7 fused to the PRV gX gene, part of the PRV gI gene, the PRV 11K gene and part of the PRV 28K gene, was used for generating a quadruple mutant containing the PRRSV ORF7.

To generate a quadruple PRRSV ORF7 containing mutant, DNA isolated from a quadruple mutant containing a β-gal insert was cotransfected with the pBQ7 into the gp50 expressing cell line MT50-3. After complete CPE became apparent, cells and supernatants were harvested and plated in serial dillutions onto MT50-3 cells under plaque assay conditions. Two days after infection progeny viruses were screened for mutant phenotypes by Bluo-Gal agarose overlay. White plaques were picked, and further plaque-purified three times.

Figure 4:
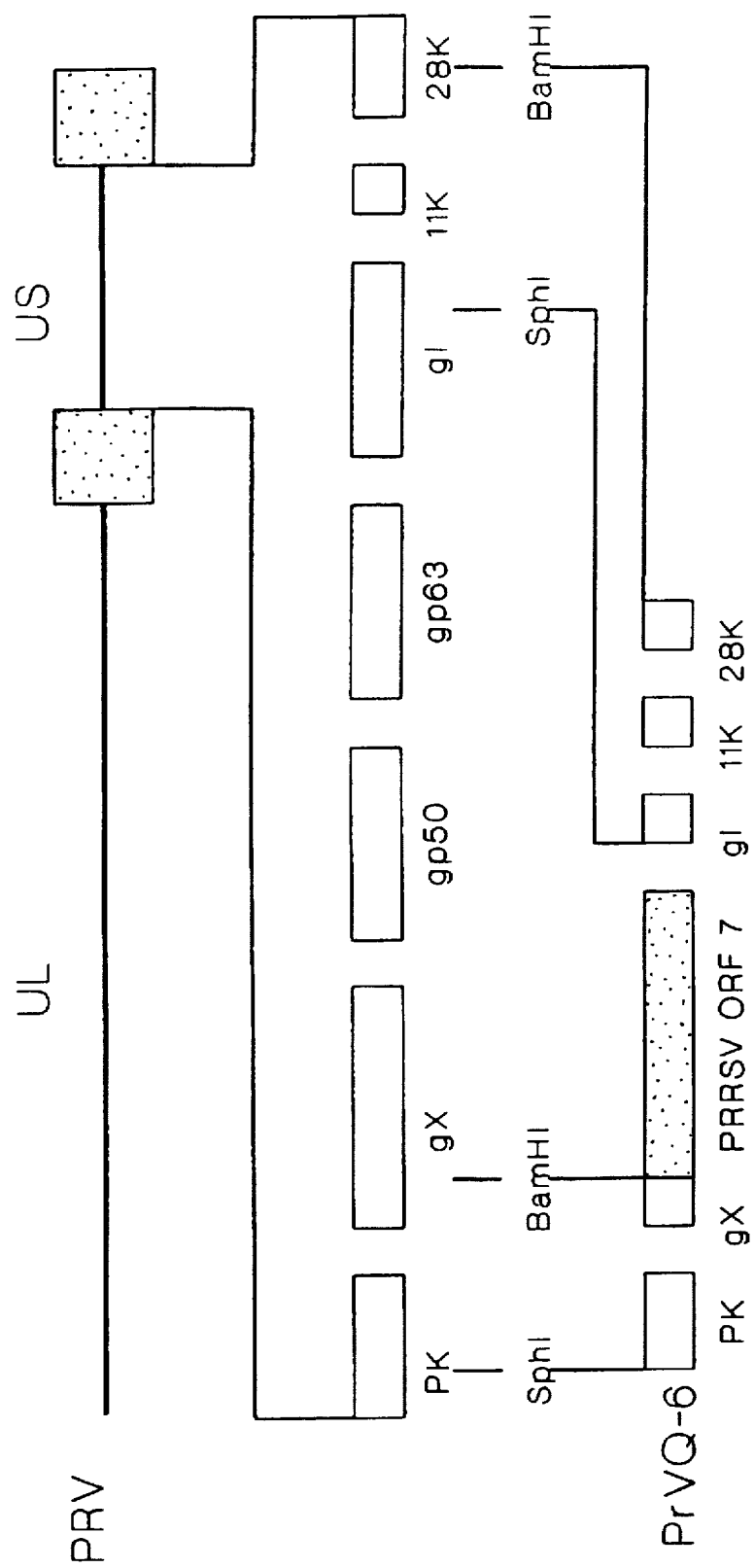

The expression of the PRRSV ORF 7 was checked by immune fluorescence by probing infected cells with the PRRSV ORF 7 specific MOAB p3-A27. A selection was made and one of the quadruple mutants containing the PRRSV ORF 7, PrVQ-6 (FIG. 4) was further used for animal experiments.

We claim:

1. A vector comprising a live pseudorabies virus, Which is able to spread from cell-to-cell in a non-complementing cell culture and which produces non-infectious progeny virions, wherein the vector harbors a gene encoding an antigen of a virus associated with antibody-dependent enhancement (ADE) of viral infectivity, wherein said virus is selected from the group consisting of FIPV, PRRSV, EAV, African Swine Fever virus, FIV and HIV.

2. The vector according to claim 1, wherein the pseudorabies virus is genotypic gp50⁻ and phenotypic gp50⁺.

3. A non-complementing cell culture comprising a live pseudorabies virus vector according to claim 1 in a cell-associated form.

4. A vaccine for the protection of a host against a virus associated with ADE of viral infectivity and for intra-nasal administration, which vaccine comprises a live pseudorabies virus vector according to claim 1, and a pharmaceutically acceptable carrier or diluent.

5. A method for immunizing a host against a virus associated with ADE of viral infectivity, comprising administering an effective amount of the vaccine according to claim 4.

6. The method according to claim 5, wherein said vaccine is administered intranasally.

* * * * *